(12) United States Patent
De Beni et al.

(10) Patent No.: US 12,245,895 B2
(45) Date of Patent: Mar. 11, 2025

(54) METHOD AND ULTRASOUND SYSTEM FOR SHEAR WAVE ELASTICITY IMAGING

(71) Applicant: Esaote S.p.A., Genoa (IT)

(72) Inventors: Stefano De Beni, Genoa (IT); Marco Crocco, Ovada (IT)

(73) Assignee: Esaote S.p.A., Genoa (IT)

( * ) Notice: Subject to any disclaimer, the term of this patent is extended or adjusted under 35 U.S.C. 154(b) by 652 days.

(21) Appl. No.: 17/493,596

(22) Filed: Oct. 4, 2021

(65) Prior Publication Data

US 2022/0104794 A1 Apr. 7, 2022

(30) Foreign Application Priority Data

Oct. 5, 2020 (EP) ..................................... 20200047

(51) Int. Cl.
*A61B 8/08* (2006.01)
*A61B 8/00* (2006.01)
*G06N 20/00* (2019.01)

(52) U.S. Cl.
CPC ............ *A61B 8/5253* (2013.01); *A61B 8/463* (2013.01); *A61B 8/485* (2013.01); *G06N 20/00* (2019.01)

(58) Field of Classification Search
None
See application file for complete search history.

(56) References Cited

U.S. PATENT DOCUMENTS

| | | | | |
|---|---|---|---|---|
| 2019/0142366 A1* | 5/2019 | Meral | ..................... | A61B 8/485 600/438 |
| 2019/0183461 A1* | 6/2019 | Sonoyama | .......... | G01S 7/52042 |

(Continued)

FOREIGN PATENT DOCUMENTS

| | | | | |
|---|---|---|---|---|
| CN | 109996498 | * | 7/2019 | ........... A61B 5/0066 |
| WO | 2019/191059 A1 | | 10/2019 | |
| WO | 2019/192970 A1 | | 10/2019 | |

OTHER PUBLICATIONS

Inoue Y, Kokudo N. Elastography for hepato-biliary-pancreatic surgery. Surg Today. Oct. 2014;44(10):1793-800. doi: 10.1007/s00595-013-0799-7. Epub Nov. 30, 2013. PMID: 24292652; PMCID: PMC4162976. (Year: 2014).*

(Continued)

*Primary Examiner* — Beniyam Menberu
(74) *Attorney, Agent, or Firm* — Dickinson Wright PLLC

(57) ABSTRACT

A method and system for two-dimensional shear wave elastography imaging (SWEI) that acquires B-mode ultrasound image of a region, selects an area of the B-mode image, automatically acquires two-dimensional shear wave elastography imaging data related to the selected area, and displays elasticity/velocity map on the selected area and optionally a reliability map. An algorithm takes as input one or combination of data sets selected from B-mode raw data or B-mode image data or elasticity/velocity map or reliability map or—raw two-dimensional shear wave elastography imaging data inside selected area, or two-dimensional shear wave elastography imaging data at an intermediate stage of processing like displacement curves over time or their peak features, and outputs the 2D coordinate of measure ROI center. Measure ROI overlapped on the B-mode image and/or on the elasticity map and/or on the reliability map is displayed. An elasticity parameter inside the measure ROI is computed, optionally weighted, and displayed.

13 Claims, 12 Drawing Sheets

(56) References Cited

U.S. PATENT DOCUMENTS

| | | |
|---|---|---|
| 2019/0261949 A1 | 8/2019 | Labyed |
| 2019/0328364 A1* | 10/2019 | Questa ................ G01S 7/52042 |
| 2019/0350559 A1* | 11/2019 | Bini ....................... A61B 8/485 |
| 2021/0212665 A1* | 7/2021 | Tsymbalenko ....... A61B 8/5223 |
| 2021/0407084 A1* | 12/2021 | Honjo ................... G16H 50/30 |

OTHER PUBLICATIONS

Extended European Search Report dated Mar. 4, 2021, which issued in corresponding EP Patent Application No. 20200047.7.

Martin A. Fischler and Robert C. Bolles, Random Sample Consensus: a Paradigm for Model Fitting With Applications to Image Analysis and Automated Cartography, Technical Note 21, Artificial Intelligence Center SRI International, Mar. 1980, 42 pages.

\* cited by examiner

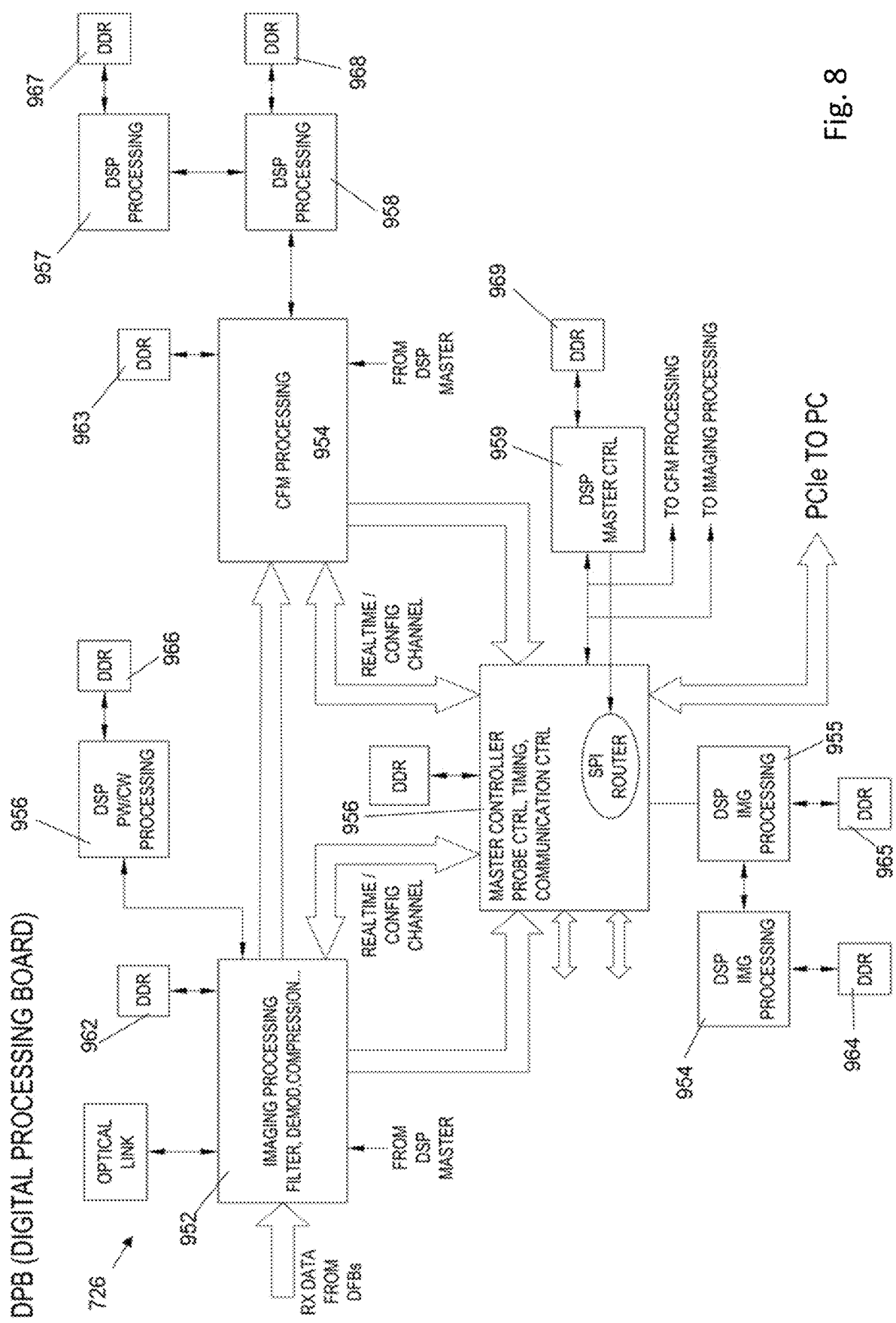

METHOD AND ULTRASOUND SYSTEM FOR SHEAR WAVE ELASTICITY IMAGING

BACKGROUND

Elasticity of soft biological tissues has been used for evaluating possible pathological conditions since the dawning of medicine. The use of manual palpations for evaluating the health condition of the tissues is still used commonly in routine medical examinations. For example, the presence of rigid masses found during routine breast examinations is often an early indication of breast cancer. Manual palpation methods however are relatively little objective and are limited to surface anatomical structures.

The methods for quantifying the elasticity or for the comparative measurement of biological tissues by ultrasounds allowing deep-tissue elasticity to be measured in the body under examination are reliable and therefore are used in clinical practice.

Unlike the traditional ultrasound imaging, such as for example B-mode that allows images to be acquired where tissues with different acoustic properties are distinguished, the methods measuring the elasticity allow tissues with different mechanical properties to be distinguished. To do this, such methods carry out an excitation of the tissues and monitor the strain response, which is related to tissue elasticity.

A type of elasticity measurement method provides to use of transverse waves, or shear waves, generated after an excitation, and are defined as Shear Wave Elasticity Imaging (SWEI). These methods generate shear waves in the tissue following an acoustic disturbance, called as shock disturbance, of the first excitation point applied by the ultrasound probe, and consequently monitor the shear waves in the regions of interest within an area along which the shear waves propagate. By measuring the displacements over time of the image or of the pixels of the image or of the pixels of a Line of Sight at a plurality of lateral positions separated by a known distance from the excitation source, it is possible to estimate the shear wave speed.

Monitoring the shear waves is carried out by tracking pulses transmitted in the region of interest and the corresponding reflected echoes measuring the displacements of the tissues along the region at which the tracking pulses are focused.

The target region at which the excitation pulse of the shear wave is directed is in many cases outside the region of interest within which the monitoring of the shear waves propagation is carried out. More generally, the area at which the shear wave is generated could also be an area placed in the region of interest. In this case, there is the need of monitoring the displacements induced by the shear waves in the tissue also in the area at which the excitation has occurred. Furthermore, also if an excitation pulse is directed to an area outside the region of interest in which the monitoring of the displacements caused by the propagation of the shear wave is carried out, due to an n azimuthal translation of a further excitation pulse in relation to the previous ones said excitation pulse could overlap the region in which one or more tracking pulses of one of the shear wave caused by one of the said previous tracking pulses are transmitted.

Actually, the measurement is indirect since the method detects the propagation speed of the shear wave in a direction substantially orthogonal to the acoustic shock disturbance of the excitation point.

The relation between speed of such shear wave and the elasticity is approximate and it depends on some assumptions about the density of the tissue under examination.

The tissue elasticity is proportional to the propagation speed of the shear wave Vs, according to the following formula:

$$E \approx 3\rho V_s^2$$

Wherein $\rho$ is the density of the tissue and it is assumed that $\rho \approx 1$, namely that tissue density is unit quantity.

The document U.S. Pat. No. 5,606,971 describes a SWE method that uses a focused ultrasound transducer that induces shear waves in a tissue by sending modulated ultrasonic pulses. The shear wave of the frequency of the modulating signal is detected. The mechanical properties of tissues under examination are evaluated based on the measured values of speed and attenuation of shear waves.

In shear wave elastography, one or a time sequence of shear wave excitation pulses are transmitted to a body to be examined to an excitation target region, which lies outside a selected Region of Interest (ROI) in which the measurement of the elasticity is aimed. The generated shear waves propagate away from the excitation target region or excitation focal point in a direction substantially perpendicular to the direction of transmission of the excitation pulses. The propagation in time of the shear wave is tracked by a series of tracking pulses interleaved to the excitation pulses of the shear waves. Due to the effect of the acoustic radiation force of the excitation pulses, the tissue in the excitation target region is displaced simultaneously establishing a shear wave. For each lateral position along the shear wave propagation direction, which is a direction perpendicular to the excitation pulse, the tissue motion induced by the shear wave will be mainly in the same direction as the one caused by the excitation pulse. Tracking pulses along several laterally staggered focal lines passing through a selected ROI can monitor such dynamic response for selected positions and lead to determining a position-specific displacement waveform representing the magnitude of tissue movement as a function of time caused by the transit of the shear wave front. Such waveforms can be computed at multiple positions along the shear wave propagation path and are processed for determining the speed of the propagation of the shear wave. Several methods have been used for processing shear wave ultrasound tracking data such as for example, Fourier transform for estimating shear wave phase velocity or shear wave amplitude peak-to-peak spatial and temporal calculations for determining shear wave propagation speed. The speed at which a shear wave propagates inside the tissue is determined by the shear modulus, shear viscosity, tissue density and shear wave frequency through some mechanical models. The stiffer the tissue is, the faster the waves move.

In an embodiment, the excitation pulses of the shear waves are transmitted in a direction, which is parallel to a depth direction inside a body to be examined, and the shear wave propagation direction is perpendicular to the said direction. The laterally staggered tracking pulses are also transmitted and received along focalisation lines, which are parallel to the direction of propagation of the said excitation pulses. Since shear waves have a certain width in the direction of propagation of the excitation pulses and in the specific embodiment in the depth direction inside the body to be examined, tracking data is acquired at different positions having different depths along each tracking line. In one dimensional shear wave elastography imaging the data at the different depth positions and along each tracking line are averaged in order to reconstruct the waveform of the displacements as a function of time along the each of the laterally staggered tracking lines. An example of such method is disclosed in document EP3240484.

Two-dimensional (2D) shear wave elastography presents 2D quantitative shear elasticity maps of tissue, which are clinically useful for both focal lesion detection and diffuse disease diagnosis. In this case, the positional data of different tracking focal points having different depth positions along each tracking line are processed separately for each depth position along the said tracking lines. A waveform of the displacement in time is thus generated for every tracking line and for every tracking focal point at a different depth along the tracking lines. The said tracking focal point are inside the area defined by a selected ROI and within the depth range corresponding to the width in the depth direction f the shear wave. In US2002/0010398, a technique according to the two-dimensional shear wave elastography imaging method is disclosed.

As it is disclosed also in document EP3240484, shear wave elastography imaging is carried out in parallel or interleaved with ultrasound morphologic imaging, so called B-mode imaging reproducing the anatomy of an area of the object to be examined. The shear wave elastography imaging is then applied to a selected sub-area, a so-called Region of Interest (ROI) of the B-mode imaged area. The anatomic images allow identifying one or more specific ROI in which shear wave elastography imaging is to be carried out.

Biopsy is the fundamental examination to evaluate liver fibrosis. The biopsy is a delicate procedure that can have serious clinical complications. In the last years technology that are now considered equivalent to the liver biopsy or that at least limit the numbers of biopsies has been developed. The most important and, considered today the gold standard, is the Fibroscan®. This technology permits a measure of the liver stiffness, computing a shear wave velocity generated by a mechanical push and tracked by an ultrasound signal. The main lack of the Fibroscan® is the missing of clear view were the measure is performed, in fact no imaging is associated with this measure. Detailed information on the Fibroscan® technology are disclosed for example at https://www.fibroscan.com/en/products.

The above disclosed shear wave 2D imaging technique allows to overcome the basic limitation of the Fibroscan system, since as it is indicated above, SWEI-2D allows to get the same measure but in a well-known position since the physician is given the possibility to view an anatomic B-mode image of the region under examination and to choose a measurement ROI, i.e. a ROI at which the elasticity measures are to be carried out so that the elasticity measurement is driven by the ultrasound image.

Although the current SWEI-2D technique overcomes the drawbacks of the Fibroscan system, due to the inhomogeneity of the tissue and thus to different propagation behaviour of the shear wave, in order to get a reliable measure, the protocol foreseen for this kind of measures provides that at least an average of ten measures is necessary. This is mainly because there is not a reliability feedback on the single measure.

A way of overcoming the above drawback in the SWEI-2D technique consists in providing a colour box which is representative of the tissue stiffness and the user can simply define a ROI on it to have the stiffness average error. The benefit is that the user has a direct feedback on the proper shear wave propagation and is able to set the ROI in a box region were the measure is reliable. This helps in limiting the number of measurements of an examination from ten to three or four and thus speed up the procedure and obtain a more reliable measure. The user places a measure ROI inside the colour box to get a measure based on the average of hundreds of points. Since the shear wave due to the inhomogeneity of the tissue can propagate not in the equal way inside the box often a second colour box encoding a reliability map is shown. Based on the stiffness image and the reliability image, the user is driven to place the measure ROI in a good portion of the image ROI.

SUMMARY

An object consists in providing more precise ways to choose the optimal measure ROI based on processes which can make use of the experience in selection of measure ROIs collected from previous examinations.

A further object consists in providing an automated method for defining and selecting an optimal measure ROI which operates on the base of the previous experience of the users.

Still a further object consists in providing an ultrasound system for carrying out SWEI 2D examinations by applying the above method providing the automatic definition and selection of a measure ROI.

In a first embodiment, a method is provided comprising:
a) Acquiring at least one B-mode ultrasound image of a region in a body under examination;
b) Selecting an area of the B-mode image (image ROI) for example by placing a selection box on the B-mode image;
c) Automatically acquiring 2DSWEI data related to the region inside the selected area;
d) Display an elasticity/velocity map on the selected area and optionally a reliability map;
e) Provide an algorithm taking as input one or a combination of two or more of the data sets according to the following list: the B-mode raw data inside the selected area and/or the B-mode image data inside the selected area and/or the elasticity/velocity map inside the selected area and/or the reliability map inside the selected area and/or the raw SWEI 2D data inside the selected area and/or the SWEI 2D data at an intermediate stage of processing like the displacement curves over time or the peak features of the displacement curves like the peak height, the peak width, the peak position in time, and providing as output at least the 2D coordinate of the center of a measure ROI and optionally the size and the shape of such measure ROI;
f) Automatically displaying the measure ROI of point e) overlapped on the B-mode image and/or on the elasticity map and/or on the reliability map;
g) Optionally tuning the measure ROI position, size and shape by the user;
h) Computing a single value of elasticity or velocity representative of the elasticity/velocity values inside the measure ROI. Such value can be the average or median of elasticity/velocity data inside the measure ROI;
i) optionally weighting the average by the values of the reliability map;
j) Display and/or save the computed average elasticity.

According to a variant embodiment, the method may comprise the following steps:
a) acquiring B-mode ultrasound images of a target region in a body under examination;
b) providing a machine learning algorithm configured and trained for analysing the acquired image data in the image ROI;

c) determining the quality of the image data in relation to the reliability of the SWEI-2D measures which can be obtained using a ROI comprising or consisting with the said image data by the said machine learning algorithm, the said machine learning algorithm having been trained using a database of known cases in which each record comprises the image data of the image ROI and the measure ROI manually selected by the user and which results has been defined as reliable;

d) Automatically determining the dimensions and the positions of the measure ROI in the image ROI;

e) automatically setting the said measure ROI for executing in it the elasticity parameter acquisition particularly according to SWEI-2D acquisition method;

f) executing the said acquisition of the velocity of propagation of the shear wave in the said measure ROI;

g) determining the elasticity parameters out of the said shear wave propagation data;

h) saving and/or displaying the said elasticity data in combination of the measure ROI and of the Image ROI.

For determining the elasticity parameters or the tissue velocity several alternative methods are known. An example of this method is disclosed in document EP3563769 or in document EP3569155.

Different parameters can be used to calculate a reliability data and the corresponding reliability map according to the above methods. The said reliability data can be calculated as a function of one or more of the following parameters: the signal to noise ratio, the numbers of outliers in the propagation curves of the shear wave, and or the statistical errors resulting from the processing of the velocity or elasticity raw data.

More details about the propagation curves of the shear wave in a ROI and in the determination and processing of outliers are disclosed in document EP3563769 and EP3569155.

According to a variant embodiment the algorithm by which determining the center, size and shape of the measure ROI meaning the ROI in which the measurement has to be carried out, can be obtained minimizing/maximizing a cost function encoding the level of reliability and/or of homogeneity of an arbitrary ROI region. The argument of the minimum/maximum of the cost function is the 2D coordinates of the ROI center and optionally the ROI size and the ROI shape.

Another option is to adopt a machine learning approach trained on the base of training set given by the couples of set of raw and/or image above described at point e) and the measure ROI described by the user.

A machine learning algorithm can also be used to calculate the minimum/maximum of a cost function.

Several different kinds of algorithm can be chosen for carrying out the above data analysis and measure ROI definition and selection. Example of machine learning algorithm models are or disclosed in https://en.wikipedia.org/wiki/Machine learning.

According to an embodiment herein, for carrying out the present method specific algorithm may be chosen such as for example classification algorithm. Within this class of algorithms there are many different kinds of algorithms or machine learning models which comprise a combination of algorithms. Some examples of the most popular classification algorithms are disclosed in https://en.wikipedia.org/wiki/Category: Classification_a lgorithms.

In relation to the training of the machine learning algorithm a further step may be carried out for filtering and or optimizing the database of the known cases in order to speed up and optimize the learning process. There are problems during the learning or training phase such as for example local minima in which the convergence process of the coefficients or weights of the functions governing the algorithm may rest providing a non-optimal configuration of the trained algorithm. According to an embodiment such kind of training database optimization may be carried out by applying to the database of the known data an optimization algorithm as the one disclosed in document EP1586076.

In relation to the term elasticity parameter according to an example embodiment of the present invention, such parameter may include one or more of the parameters of the group comprising: velocity of the shear wave propagation, Young's modulus, shear modulus, bulk modulus, Poisson's ratio, Lame's first parameter, P-wave and combinations of these parameters. This meaning of the term elasticity parameter applies for the description and for the claims.

In relation to the term box, this term indicates an area on an image delimited by a perimetral contour which can have different forms according to different polygons. The box can be drawn on an image or an image of a box can be superimposed to an image by drawing tools or visualization tools controlled by the user and the area of the image delimited by the box peripheral contour can be selected for carrying out operations on the said image.

According to a further improvement by an example embodiment of the present invention, the appearance parameters of the pixels as a function of the calculated elasticity parameters can be a different colour level scale as the grey scale used for displaying the image data in the B-mode image.

The colour scale can be chosen as being a monochromatic scale different as grey, for example red, blue or green or a polychromatic scale.

In one embodiment the appearance of the pixel or the pixels for representing one or more elasticity parameter determined in a measurement ROI selected within an imaging ROI as a function of the measurements at the two or more tracking focal points is monochromatic and the different values of the elasticity parameter are correlated to different shades of one colour.

In one further embodiment the appearance of the pixels for representing the elasticity parameter determined in a measurement ROI define and selected according to one or more of the above mentioned embodiments is displayed by a polychromatic scale and the different values of the elasticity parameter are correlated to different colours.

According to an embodiment the elasticity parameter determined from an automatic selected measure ROI is displayed together with a reliability parameter.

According to an embodiment herein and as it will appear with more in detail from the following description, the algorithm by which determining the center, size and shape of the measure ROI meaning the ROI in which the measurement has to be carried out, can be obtained minimizing the number of outliers in the area of the image which will be chosen as the area corresponding to the measuring ROI.

The meaning of outliers is explained with more detail in the published application EP3569155.

FIGS. 9A to 9C show a simplified diagram of a probe emitting tracking pulses focalized along three different lines of sight indicated by T1, T2 and T3 and a shear wave excitation pulse 10. The tracking pulses and the shear wave excitation pulse are generated by an ultrasound probe 20 comprising an array of electroacoustic transducers.

FIG. 9B shows the principle of the one-dimensional shear wave elastography for each tracking line the displacement curve as a function of time is indicated. The displacement curves as a function of time along the line of sight at which each tracking pulse is focused are obtained by averaging the displacement data measured at different ranges of depth, i.e. at different segments of predetermined length of the line of sight, so that for every line of sight only one displacement curve is determined.

The time of arrival of each shear wave at a certain location can be estimated from the maxima of the displacement curves carrying out a linear regression of the time of arrival of the shear wave at the maxima of the said displacement curves.

Ultrasound echoes reflected and received by the probe are cross correlated in time after beamforming in order to determine the displacement of the tissue caused by the passage of the shear wave and thus the displacement curves in FIG. 9B. The result of one-dimensional shear wave elasticity imaging is a unique velocity value for the shear wave in the region of interest and thus a unique value for each elasticity parameter of the tissue in the region of interest which can be calculated starting from the velocity of the shear wave.

FIG. 9C show the ideal condition of the shear wave velocity estimation using linear regression. The slope a of the regression line is the inverse of the velocity of propagation of the shear wave and the linear regression is carried out on the data pair of the determined time of arrivals of the peaks of the displacement curves in FIG. 9B and the position coordinate of the corresponding line of sight or tracking line T1, T2, T3 in the direction of propagation 11 of the shear wave or in a direction perpendicular to the line of sights or tracking lines T1, T2, T3.

FIG. 10A shows an example of how the displacement curves as a function of time may appear in a real case in comparison to the theoretical case illustrated in FIG. 9B. The example is extremely simplified in order to better appreciate the technical principle.

As it is shown the displacement curve as a function of time measured along the tracking line T3 shows a local maximum at L1 and at L2. The local maximum at L1 represents an outlier of the distribution of the data pairs relating to the time of arrival as a function of the position of a tracking line and is indicated by OUT1.

Applying a traditional regression algorithm would lead to a not precise determination of the velocity of the share wave propagation and of the elasticity parameters calculated from it.

Each of the data pairs relating to each of the local maxima in the displacement curve as a function of time may be considered as valid data for finding a regression line. According to an embodiment, the best fitting regression line is determined by applying on the data pairs relating to time of arrival and corresponding position of the tracking line in the lateral direction a RANSAC algorithm. This algorithm operates by calculating every possible regression line and then choosing the one considered to best fit the data applying at least one criterion or a combination of criteria.

FIGS. 10B and 10C show the result of the processing by the RANSAC algorithm by considering two different criteria respectively. In FIG. 10B the criteria for determining the best regression line was to minimize the number of outliers. The regression line thus is close to three of four local maxima of the three displacement curves.

The diagram of FIG. 10C shows the result when the criteria for choosing the best fitting regression line is set as the line minimizing the quadratic error on the data points.

In FIGS. 10B and 10C, a point falling at a great distance from the regression line is defined as an outlier from the regression line computed according to respectively one of the two alternatives disclosed above. The quality of a velocity or elasticity measure based on a regression line in a region is somehow related to the number of outliers which are present in the measured displacement data along the tracking lines. Furthermore, when considering the two algorithms also a statistical parameter indicating the fitness or the precision of the processed data is obtained by the algorithm. This fitness or precision parameter can be a measure for a reliability parameter of the velocity or elasticity data determined for the corresponding ROI.

According to an embodiment not shown these two criteria could also be combined and optionally also differently weighted in their combination.

The RANSAC algorithm is per se known in the art a generic description of the algorithm can be found in Martin A. Fischer and Robert C. Bolles SRI International, Random Sample consensus: A Paradigm for Model Fitting with Applications to Image Analysis and Automated Cartography, in Communication of the ACM June 1981 Volume 24 Number 6 and in many other publications.

According to an embodiment an ultrasound system is provided for shear wave elasticity imaging (SWEI) comprising:

An ultrasound probe;

An ultrasound image acquisition section configured to acquire at least ultrasound anatomic images such as B-mode images;

An image generation unit for generating the B-mode image;

A display for displaying the B-mode image;

An image ROI selecting parameter for selecting a region in the B-mode image;

A B-mode image data analyzer executing a machine learning algorithm for determining the most reliable region of the image ROI relating to the measurement of shear wave propagation behavior, and particularly shear wave propagation velocity;

An automatic measure ROI setting unit for defining and selecting as the measure ROI of the shear wave propagation behavior and particularly shear wave propagation velocity the said most reliable region of the image ROI determined by the B-mode image data analysis;

A shear wave excitation pulse generation unit for transmitting said shear wave excitation pulses at a shear wave excitation region or point beside or inside the said measure ROI;

An ultrasound shear wave tracking section configured to transmit and receive ultrasound tracking beams in the said measure ROI;

A signal processing unit of the ultrasound received tracking beams, which unit is configured to calculate elasticity parameter values in the selected region of interest;

A display unit for displaying the calculated velocity or elasticity parameters in the said measure ROI optionally in combination with a reliability parameter of the said velocity or elasticity parameter.

According to an embodiment, the ultrasound system further comprises

An image generation unit for graphically representing the elasticity parameter values in the selected measure ROI in an elasticity image;

An image combination unit for combining the image elasticity image with the anatomic B-mode image of the said selected measure ROI;

An image display receiving the image data from the image combination unit and displaying the combined image.

According to an embodiment, the ultrasound system comprises an ultrasound probe;

An ultrasound transmit-wave generator and an ultrasound transmit beamformer;

An ultrasound receive-beamformer;

ultrasound receive signals processing unit for generating ultrasound image data;

a shear wave excitation pulse generator and a shear wave beamformer;

a display for displaying an image;

a selection tool for selecting a region of the image by showing the limits of the said region on the said image on the display;

a central control unit comprising:

a memory storing program instructions;

at least one processor that executes the program instructions to:

a) Automatically acquiring 2DSWEI data related to the region inside the box by generating an acoustic excitation ultrasound pulse directed at an excitation region or point beside or inside the said measure ROI, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;

generating ultrasound tracking beams focused along different tracking lines which are at different predetermined laterally staggered distances one from the other and from the said excitation region or point and which encompasses the said measure ROI;

process the ultrasound echo signal reflected at different tracking focal points distributed along the said tracking lines for calculating the values of elasticity parameters in the said ROI;

b) Display an elasticity/velocity map on the box region and optionally a reliability map.

c) carrying out an algorithm taking as input the B-mode raw data inside the box and/or the B-mode image data inside the box, and/or the elasticity/velocity map inside the box and/or the reliability map inside the box and/or the raw SWEI 2D data inside the box and/or the SWEI 2D data at an intermediate stage of processing like the displacement curves over time or the peak features of the displacement curves like the peak height, the peak width, the peak position in time, and providing as output at least the 2D coordinate of the center of the measure ROI and optionally the size and the shape of the measure ROI.

d) Automatically displaying the measure ROI of point c) overlapped on the B-mode image and/or on the elasticity map and/or on the reliability map.

e) Optionally tune the ROI position, size and shape by the user.

f) Compute the average elasticity inside the ROI;

g) optionally weighting the average by the values of the reliability map;

h) Display and/or save the computed average elasticity.

According to an alternative embodiment, the said at least one processor executes the program instructions to:

define an image ROI in the ultrasound image;

automatically define and select a measure ROI in the said image ROI by executing a machine learning algorithm determining defining the dimensions and the position of the said measure ROI as the result of a reliability analysis of the image data in the image ROI;

generate an acoustic excitation ultrasound pulse directed at an excitation region or point beside or inside the said measure ROI, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;

generate ultrasound tracking beams focused along different tracking lines which are at different predetermined laterally staggered distances one from the other and from the said excitation region or point and which encompasses the said measure ROI;

process the ultrasound echo signal reflected at different tracking focal points distributed along the said tracking lines for calculating the values of elasticity parameters in the said measure ROI;

calculating the elasticity parameter value and/or distribution in the measure ROI;

representing the elasticity parameter in the said measure ROI on the Image ROI by a chromatic scale of the pixel appearance so that the value of the elasticity parameter is indicated by a color of the said scale;

combining the image ROI with the elasticity parameter by displaying the pixels inside the measure ROI with the color corresponding to the determined elasticity parameter according to the color scale;

an image display receiving the combined images and displaying the said combined images.

BRIEF DESCRIPTION OF THE DRAWINGS

FIG. 8 illustrates a block diagram of the digital processing board.

DETAILED DESCRIPTION OF EXAMPLE EMBODIMENTS

Figure 1:
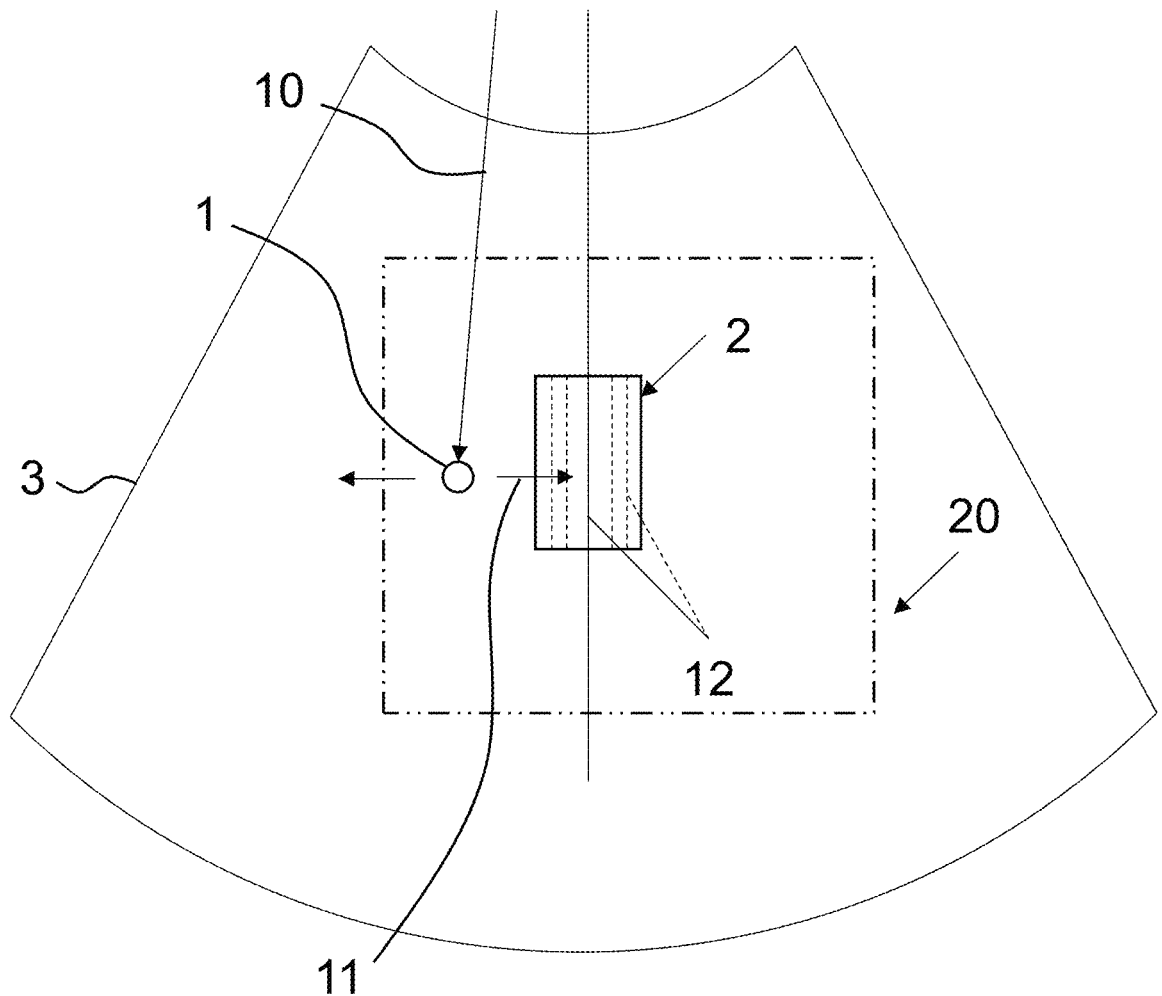
FIG. 1 is a simplified representation of an ultrasound image in which there is shown the region to which the shear wave excitation pulse is applied and the region of interest in which the shear wave propagation is tracked.

FIG. 1 shows the image representing schematically the steps of the method according to an example embodiment of the present invention, an anatomic image of a target region 3 is acquired. On the B-mode image 3 the user defines a region of interest 2 through a gate, in which region of interest 2 the tissue elasticity is desired to be indirectly measured.

An imaging region of interest 20 may be selected helping in reducing the image dimensions and thus the number of pixels to be processed.

Inside the said image ROI a measure ROI 2 is selected in which the process of determining the parameters of the shear wave propagation and particularly shear wave velocity is to be measured.

The region of interest 2 may have any shape, preferably a rectangular shape or as a section of an annulus or a circular shape, and preferably it has a predetermined size for the end user. The user can place the region of interest 2 where desired.

During the dedicated acquisition, the B-mode image is still, or "frozen", and it can be removed from such condition only after having performed the transmission-reception sequence along the tracking lines which is characteristic of shear wave elastography process.

Once having defined the region of interest 2, the shear wave elasticity imaging process starts. The elasticity parameters of the region of interest are determined by tracking the shear wave passage along the region of interest and as a function of the displacements caused by the shear wave propagation to the material, i.e. the tissue in the region of interest.

Once a measurement has ended, the image can be "unfrozen" such to allow a new shot and a new acquisition, till leaving the mode.

Once the region of interest 2 is defined, an excitation point or region 1 is defined within the acquired B-mode image 3.

According to an embodiment the excitation point or region 1 is placed outside the region of interest 2 and preferably laterally displaced relatively to the region of interest when referred to the direction of propagation of the tracking beams 12.

Therefore, a focused ultrasonic beam 10 is generated for acoustically generating an excitation pulse at point or region 1, to cause the generation of a shear wave 11. The shear wave 11 originates in the excitation point or region 1 and has a propagation direction substantially perpendicular to the direction of propagation of the ultrasonic excitation beam 10, in the two opposite departing directions. The excitation point 1 is placed such that the shear wave 11 passes through the region of interest 2. The generated shear wave 11 is measured at a plurality of lines of sight 12 which are focused such that they pass inside the region of interest 2 at different predetermined lateral distances from the said excitation point 1. FIG. 1 shows the line of sight under examination as a continuous line 12, while the other lines of sight are broken lines.

By the measurement of the passage of the shear wave on all the tracking lines or lines of sight 12 the propagation speed of the e measured shear wave is calculated.

In normal operation according to the state of the art, the choice of the measure ROI 2 is carried out manually by a doctor or a user of the ultrasound system. The precision of the elasticity measure inside the measure ROI is strongly dependent on the tissue quality corresponding to the image in the measure ROI. Currently the selection of the measure ROI is carried out manually based on the experience of the user which can see the anatomical B-mode image and thus estimate tissue regions in which inhomogeneity is low and thus the propagation velocity of pressure waves inside the said tissue region can be assumed as not being subject to aberrations.

The said manual choice obliges to carry out several repetitions of the measure in order to calculate a mean value of the elasticity coefficient of the tissue in the selected measure ROI which is based on a sufficiently large number of measures and providing a statistically reliable estimation.

This kind of proceeding results in lengthening the duration for the examination.

According to an example embodiment of the present invention the selection of the measure ROI is carried out preferably automatically by using an algorithm which determines an optimized measure ROI relatively to its position in relation to the B-mode image (the anatomic image) and/or to the dimension of the said ROI (i.e. the area) and/or the shape of the boundaries of the said ROI.

Different kinds of algorithms may be used which are of different nature.

As it will be clear from the following non-limiting examples, one solution in accordance with an example embodiment uses an analytic algorithm or computational method such as for example an optimization algorithm, in particular a cost function. In the case of a cost function the maximum or the minimum of the cost function has to be determined.

An alternative solution in accordance with another example embodiment is based on a machine learning algorithm which is trained on a database of known images and known measure ROI selection in the said images and known fitness of the elasticity coefficients obtained by carrying out SWEI 2D inside the said measure ROI.

Figure 2:
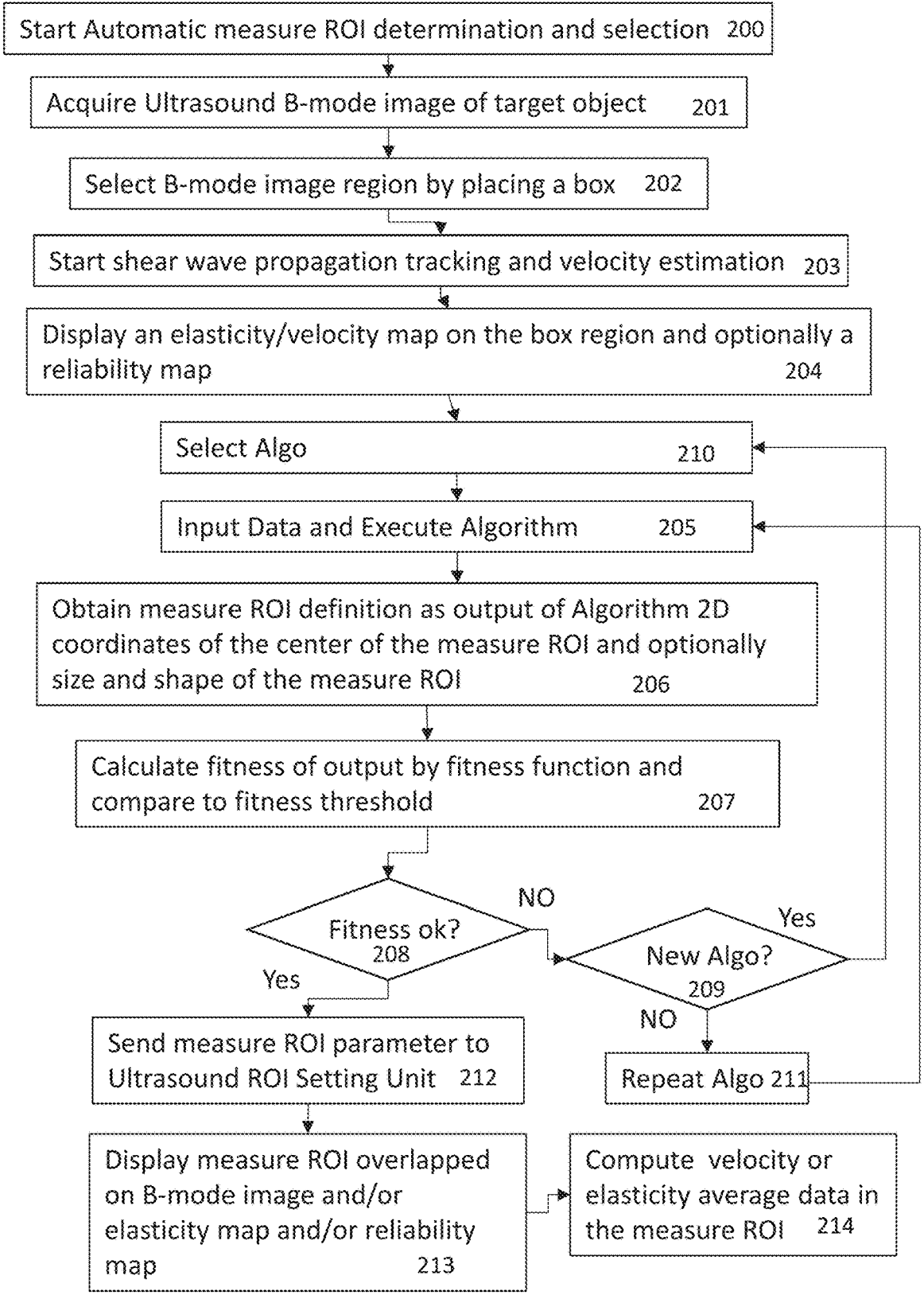
FIG. 2 is a flow diagram showing the automatic definition and setting of a measure ROI for carrying out a shear wave 2D elasticity measurement process. The steps of training database generation process according to an embodiment of the present invention.

Considering the first example, FIG. 2 shows a flow diagram of the steps for carrying out this method.

At step 200 the automatic measurement of the ROI process is started. In a first step the ultrasound system is set in order to acquire a B-mode image of a target region of a body at step 201. Acquisition is carried out according to known techniques and the resulting image is displayed on a monitor of the system.

At step 202 a ROI is selected on the displayed image by means of selection tools. This can be done according to different ways. According to one embodiment the ROI corresponding to a region of the displayed image is selected by drawing a line along a closed path which encircles the selected region of the displayed image. The line along the closed path is the contour of a selection box and the shape of the contour can be circular, polygonal, curved, regular or irregular, in particular the selection box can show a rectangular form. The said line can be drawn by drawing tools provided in the User Interface with the system, such as a mouth, a virtual pen, a finger.

Once the region of the displayed image is selected by placing the above selection box on the displayed image, the shear wave imaging process is commenced for shear wave propagation tracking and velocity estimation (step 203) according to the examples disclosed above and for example to the disclosure of documents EP3563769 and EP3569155. An elasticity/velocity map and optionally a reliability map can be displayed on the box region (step 204).

The B-mode imaging process and the shear wave imaging process provides for different data sets like for example the ones according to the following list: B-mode raw data inside the box and/or the B-mode image data inside the box, and/or the elasticity/velocity map inside the box and/or the reliability map inside the box and/or the raw SWEI 2D data inside the box and/or the SWEI 2D data at an intermediate stage of processing like the displacement curves over time or the peak features of the displacement curves like the peak height, the peak width, the peak position in time.

One of the above mentioned data sets or a combination of two or more of the above mentioned data sets can be used as input data of an algorithm (e.g., step 205) for determining as a function of the said data the position and/or the size and/or the shape of a measure ROI in which the mean elasticity or the mean velocity parameters calculated in the said measure ROI are expected to be the more reliable than the ones in the other regions of the image.

Also the measure ROI can be defined by a closed line which represents the peripheral limits of a selected region in the displayed image and which can have any kind of shapes similarly to the selection box.

Selecting the algorithm according to the present step 210 means to provide an analytic algorithm for processing the above mentioned input data giving as an output at least the 2D coordinate of the center of the measure ROI and optionally the size and the shape of the measure ROI as indicated by step 205 and step 206.

In one embodiment, the analytic algorithm (step 210) can be a cost function, the minimum of which or the maximum of which is to be determined.

Figure 10A:
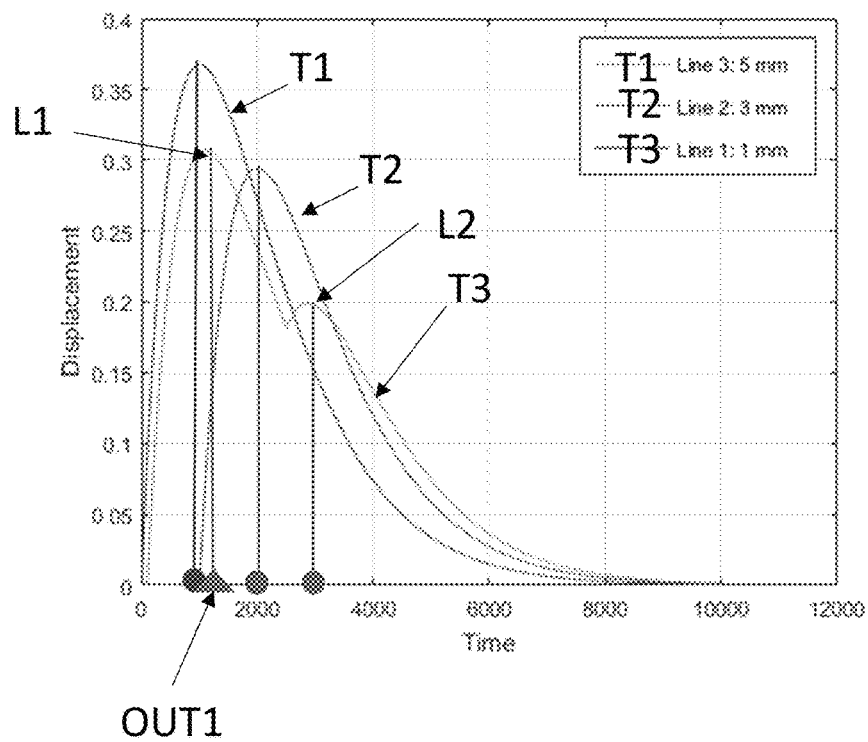
FIG. 10A represents the generation of local maxima determining the generation of outliers in the data to which linear regression is applied.
Figure 10B:
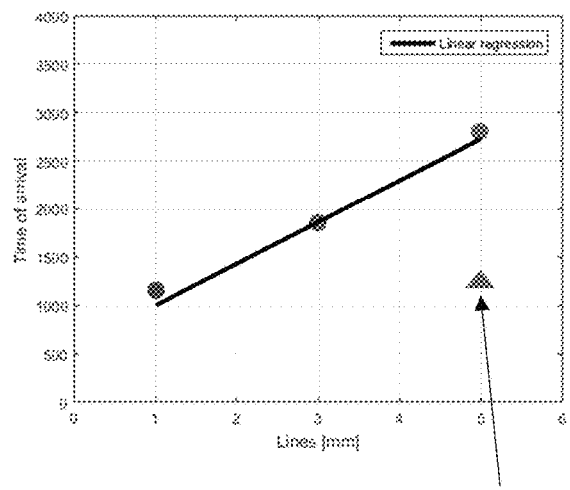
FIG. 10B is the result of applying one embodiment of the method in which all the data pairs relating to all the local maxima are considered and the regression line is calculated by using a RANSAC algorithm, the criteria of choosing the regression line which best fits the data being in this case the reduction of the number of the outliers.
Figure 10C:
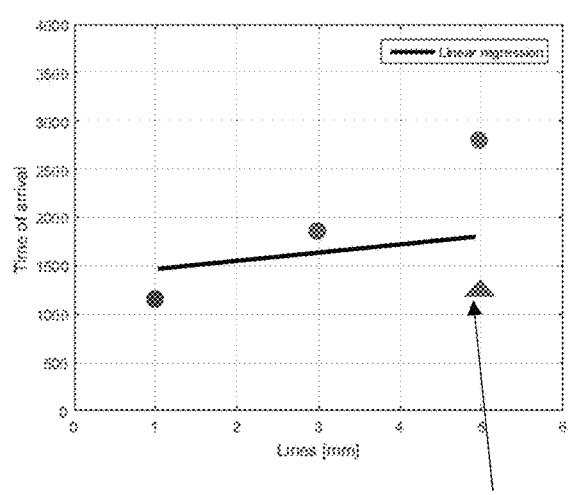
FIG. 10C is a diagram analogous to the one of FIG. 10B in which the criteria of choosing the best fitting regression line is the one of the regression line minimizing the quadratic error of the inliers.

According to an embodiment the cost function can be a function of the peak position in time in the displacement curves disclosed above with reference to FIGS. 9a, 9b, 9c and 10a, 10b, 10c. More precisely according to the above exemplary embodiment, the cost function minimizes the number of outliers in the calculation of the regression line in the time of arrival/scan line position diagram as shown in the examples of FIGS. 10a to 10c.

In a variant embodiment other optimization or minimisation/maximisation criteria can be used for choosing and configuring a cost function, like for example the optimization of the Signal to Noise Ratio of the data of one or more of the above listed data sets in the region destined to be defined as the measure ROI, the maximization of the mean reliability of the velocity or elasticity data in the measure ROI or the minimization or maximization of one of the further indicated data sets in the region which is determined as the measure ROI or a combination of the above criteria, for example, maximization of Signal Noise Ratio and the to minimization of the number of outliers, or other combination of maxima or minima of the parameters of one or more datasets in the region destined to be determined as the measure ROI.

After having calculated the position and/or size and/or shape of the measure ROI the mean elasticity or velocity parameters is determined in the said region of the measure ROI by means of the shear wave imaging described above in connection with step 203.

At step 207 a fitness of the said mean elasticity or mean velocity parameter can be determined according to a fitness function which according to an embodiment can be the mean reliability of the said velocity or elasticity parameter. This value can be compared with a fitness threshold in order to determine if the fitness, as for example the mean reliability parameter can be considered satisfactory or not as indicated at step 208. If the fitness or reliability does not satisfy the condition set by the threshold, two alternatives are possible as shown at steps 209 and 211. The computation is carried out again using the same algorithm or a different algorithm is selected from a library of alternative algorithms and the steps from 210, 205 to 208 are repeated. The loop may be carried out till the fitness like the mean reliability satisfy the condition set by the threshold. In order to avoid infinite loops, in a possible embodiment a maximum number of loops is set. In reaching the maximum number of loops the repetition of the steps 209, 211, 210 and 205 to 208 is stopped and the mean velocity or elasticity is chosen as the one having the best fitness, like the highest reliability among the elasticity or velocity parameters determined in the different repetition cycles. According to an embodiment, the said selected mean velocity or mean elasticity data can be further associated with an indication that the fitness, as for example the reliability is low according to the fitness/reliability evaluation criteria, for example the comparison with the threshold by giving a particular optical aspect to the displayed values for elasticity or the velocity parameter and/or by adding the fitness or the reliability value for the said velocity or elasticity parameter.

As indicated with step 212 the measure ROI parameter, once determined is sent to the ultrasound system and particularly to a section of the control unit of the ultrasound system in a ROI setting unit as indicated by 212. As indicated by 213, the measure ROI of point can be displayed overlapped on the B-mode image and/or on the elasticity map and/or on the reliability map. Velocity or elasticity average data inside the measure ROI can be computed as indicated by 214.

Figure 3A:
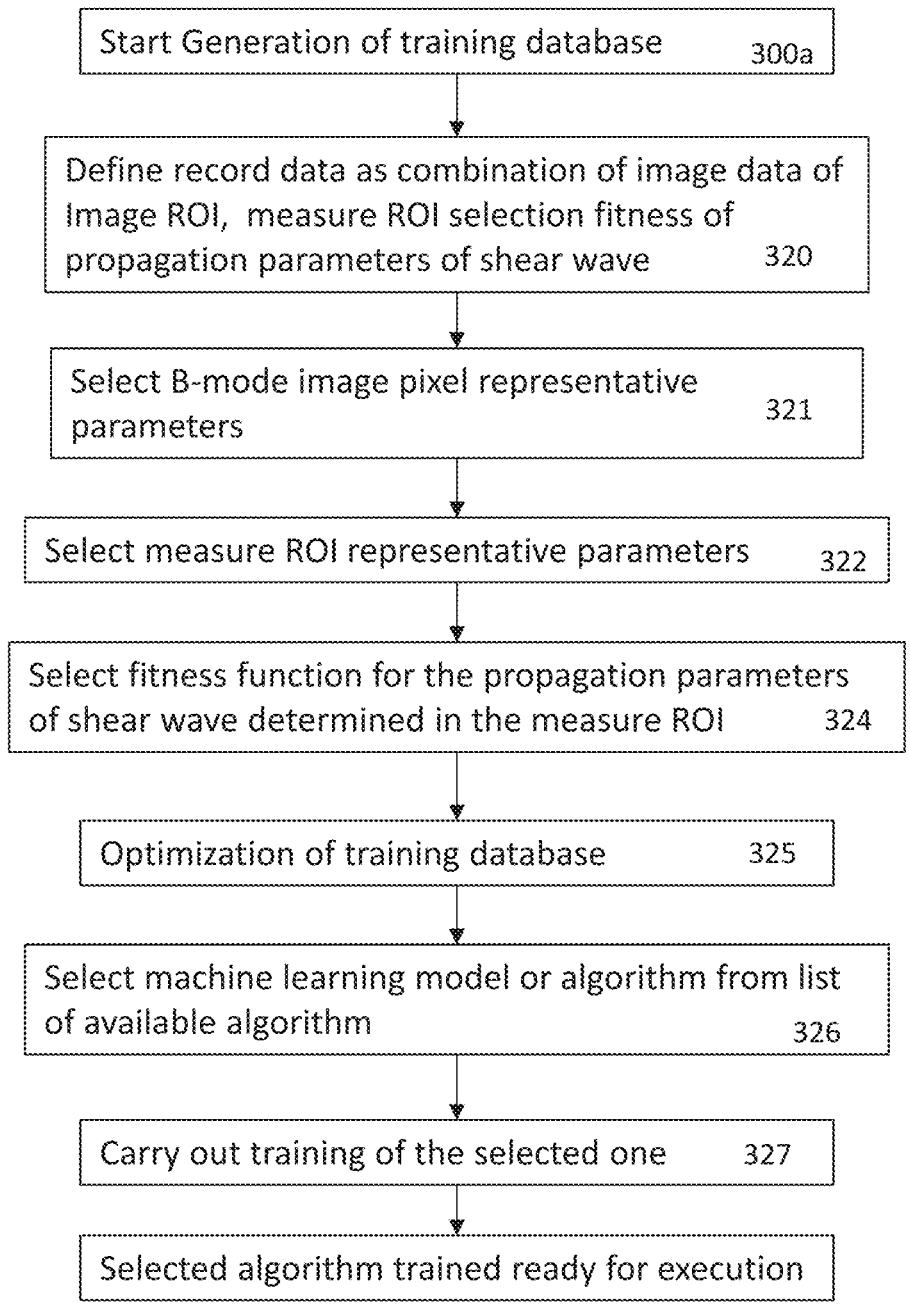
FIGS. 3a and 3b are a flow diagrams showing the steps of training database generation process according to an embodiment of the present invention and the automatic definition and setting of a measure ROI for carrying out a shear wave 2D elasticity measurement process according to said embodiment.
Figure 3B:
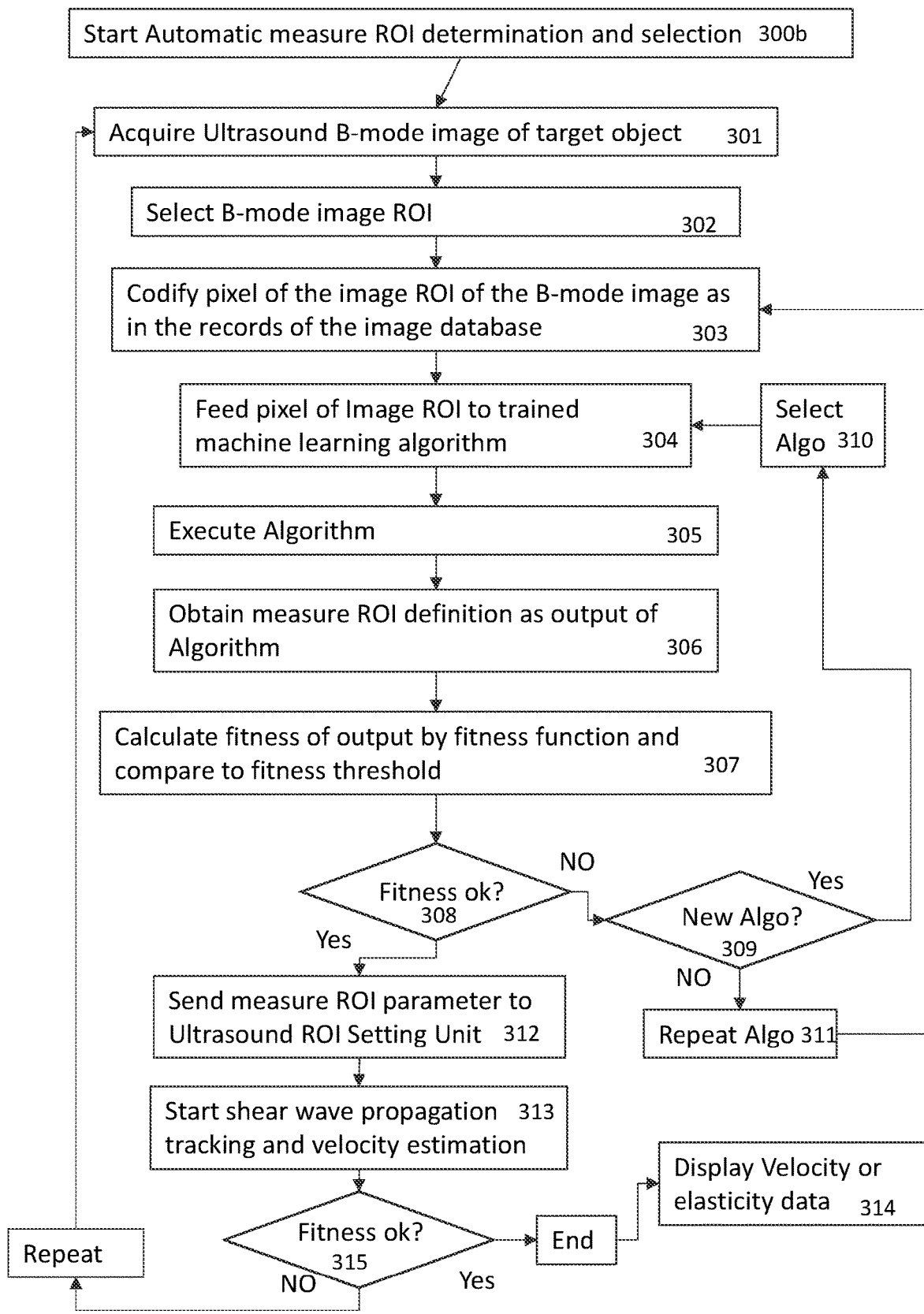

FIGS. 3a and 3b show the flow diagrams of respectively the steps of training database generation process according to an embodiment of the present invention and the automatic definition and setting of a measure ROI for carrying out a shear wave 2D elasticity measurement process according to said embodiment.

The first step of the method relates to generating a training database for training one or more machine learning algorithm chosen from a very large number of such kind of algorithm.

Most suitable algorithm to be used for determining the position and dimensions of the measure ROI could be a predictive algorithm or a classification algorithm.

Also a combination of two or more algorithms can be used for determining the said measure ROI.

According to an embodiment, once the position and the dimensions, i.e. the limits of the measure ROI has been determined the US apparatus and specifically the control unit of the apparatus may be automatically driven to set the measure ROI and carry out the shear wave excitation and the tracking of the shear wave propagation inside the said measure ROI in order to determine shear wave velocity and elasticity coefficient of the tissue in the said measure ROI and thus in the corresponding region of the target body.

FIG. 3a is a flow diagram showing an embodiment of the process for generating a training database and for training an algorithm such as for example a classification algorithm or other kind of algorithms.

Starting the process at step 300a a definition of the data set that each record shall contain is made at step 320. In the embodiment of FIG. 3a, the following data is considered relevant: The image data of the image ROI, which may be defined as the parameters determining the appearance of a pixel in a B-mode image. These parameters can be in the form of vectors and comprising also parameters describing the appearance or the features of one or more surrounding pixels optionally weighted in relation to the distance of the pixel of which these represents the surrounding ones.

Furthermore a function describing the fitness or reliability value of the propagation parameters of the shear wave measured by the SWEI 2D method inside a certain selected measure ROI, as well as optionally also the parameters describing the position and the dimensions of the measure ROI relatively to a certain image ROI or to the whole image.

Several different coding criteria of the said parameters are available and the skilled person can make use of any one of these criteria without exercising any inventive skill or without the need to go further from usual tasks.

Step 321 to 324 allow to make a selection among the defined parameters at step 320.

In the shown embodiment a training database optimization step 325 is provided which could be an optional step. Many different methods of optimizing the training database of a machine learning algorithm are known.

A particularly suitable example is disclosed in relation to FIG. 4 in the following. This method is not to be considered limitative of the scope of protection but is only an example on how to carry out the training database optimization.

Once a training database is generated one or more machine learning algorithm can be selected among the different available algorithms at the state of the art which are best fit for solving the present problem as it is shown at step 326.

At 327 a step of training the selected one or more algorithm which can then be stored as ready to be used for processing the input data in order to provide the position and the dimensions of a measure ROI in a certain image ROI or image for carrying out SWEI 2D elasticity measurements.

FIG. 3b shows a flow diagram of an embodiment of a process to automatically determine the measure ROI by using one or more of the algorithms trained for example according to the process of FIG. 3a and for setting the said measure ROI manually or automatically at the ultrasound system for carrying out elasticity measures by a SWEI 2D method in the said measure ROI.

Step 300b starts the process for automatic determination of the measure ROI. At step 301 firstly a B-mode image of a target body or region is acquired. On this image it is possible but not necessary to define an image ROI as indicated by the step 302. Using an image ROI could reduce the computational burden and the duration of the computation since the process could be limited to the said image ROI.

The pixel of the B-mode image or the pixel of the image ROI are subjected to coding by the same parameters chosen for coding the pixel in the records of the training database as indicated at step 303. The thus coded image data are fed to an algorithm as indicated at step 304 and the algorithm is executed as indicated at step 305. The data could be fed at the same time to more than one trained algorithm so that the processing with each of the more than one algorithms should be carried out in parallel furnishing results which fitness can be compared and which results could be also combined together.

The algorithm(s) provide as an output a measure ROI dimension and a measure ROI position as indicated at step 306. For the output data provided by each algorithm executed a fitness value is then calculated using the same fitness function used for the fitness value of the records of the training database as indicated by step 307.

An evaluation of the fitness data is made at step 308. Here if the fitness value is not satisfactory, for example lower than a threshold value it is possible to choose at step 309 either to repeat with the same algorithm the processing as indicated by step 311 or to select a new algorithm as indicated by step 310 if more than one kind of algorithm has been trained and is available stored in a memory of the system.

If the fitness value is ok as indicated by step 312 the parameters defining the measure ROI are sent to a ROI setting unit of the ultrasound system and after the setting of the said measure ROI the shear wave excitation and the shear wave propagation tracking inside the said measure ROI is started as indicated by the step 313.

At step 315 a further reliability or fitness value can be determined for the elasticity parameter or the velocity determined by the shear wave tracking process. If the fitness value is lower than a certain threshold the process may be repeated from the start. If the fitness value is higher than a certain minimum threshold value, then the process is ended and the velocity or elasticity data are displayed as indicated at 314. The elasticity parameters can be displayed either as numeric data or by using a colour palette in which each colour is representative of a certain value of the elasticity parameter in the measure ROI.

Figure 4:
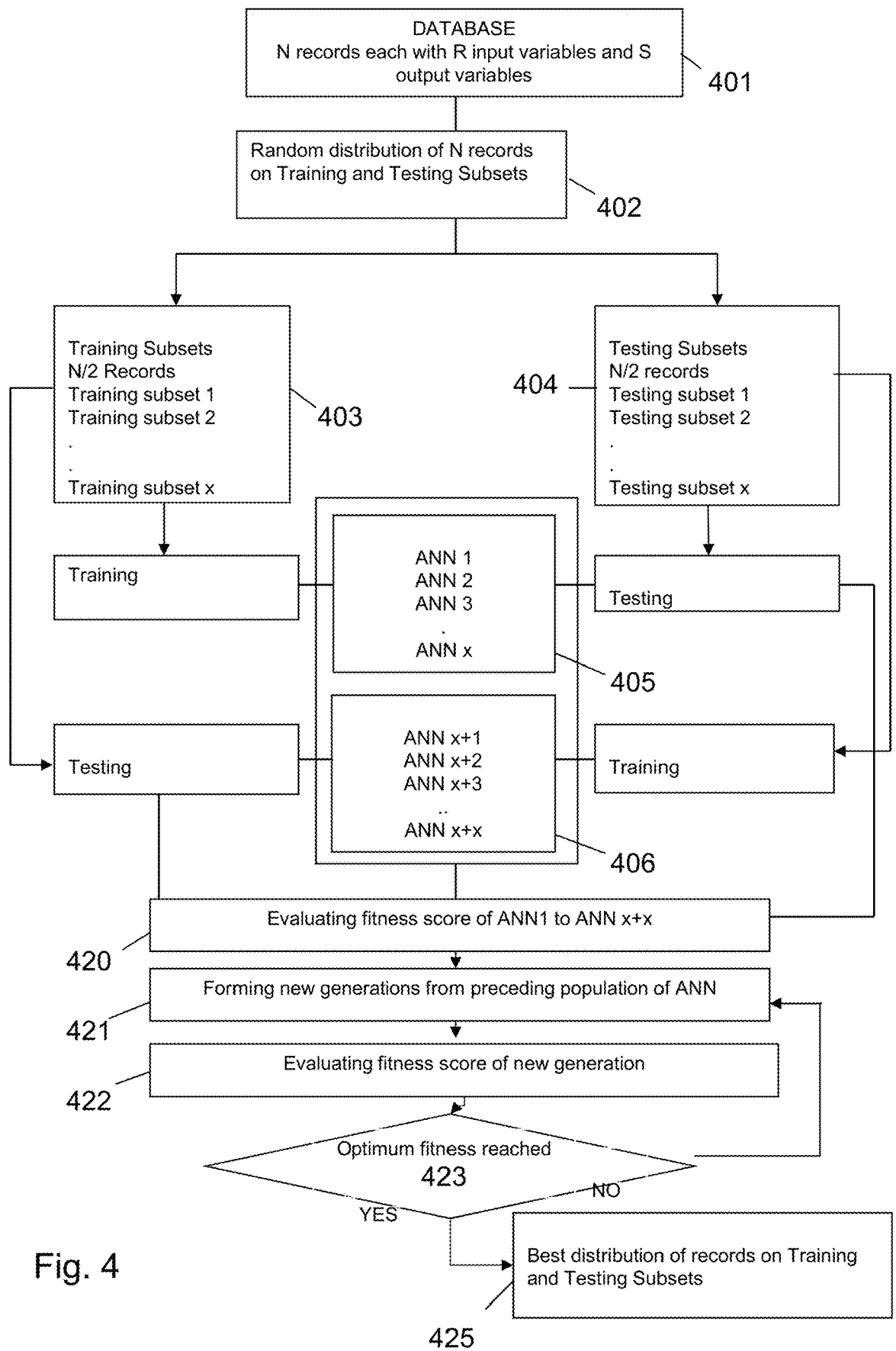
FIG. 4 is a flow diagram showing an embodiment of a training database optimization method.

FIG. 4 depicts an exemplary approach according to an embodiment of the present invention for optimizing the distribution of the records of the complete database 401 onto training subsets 403 and testing subsets 404 in such a way so as to obviate the limits of the conventional method using non optimized or else optimized databases. The starting point is again a complete data set indicated at 401 comprising, for example, N records having R known input variables and S known output variables related to the input variables according to some functional, relational or other dependence.

The process of optimization of the distribution begins with a random distribution 402 of the N records onto a training subset 403 and a testing subset 404. This step may be repeated several times in order to generate a population of prediction algorithms, for example different artificial neural networks ANN 1 to ANNx 405. Each member of such population is thus trained and tested using a different random distribution of records, indicated in FIG. 4 by the indexed training and testing subsets 1 to x. Training and testing subsets may be also inverted as described above to generate ANNs x+1 through x+x 406.

This first population of trained and tested prediction algorithms comprises a certain number of prediction algorithms, each one being representative of a certain distribution of the database 201 records onto a training and a testing set.

Further, the population of prediction algorithms can be fed to an evolutionary algorithm such as, for example, a genetic algorithm, which generates from the original parent population 405, 406 a series of generations according to certain rules, which try to emulate the natural genetic development of species, similar to the way in which artificial neural networks try to emulate basic human cognitive functionalities.

An evolutionary algorithm can thus evaluate the fitness of the single prediction algorithms, such as, for example, single artificial neural networks, of a parent population, by calculating the error in predicting the known output variables of the testing sets on the basis of the corresponding input variables of the testing set. This process is illustrated in FIG. 4 at 420. Such fitness is referred to as a "fitness score." The fitness score can then be used as one of the basic parameters for defining recombination rules for further generations.

The evolutionary algorithm can provide, for example, for the formation of a "child" generation of prediction algorithms 421, based on a new distribution of records onto the training and testing set, such distribution being obtained by merging or mutating the distribution of records of the parent algorithms. The individuals, namely the single prediction algorithms of this new child generation, can again be evaluated relative to their fitness score, 422 in FIG. 4, and the child population used to generate a new "grandchild" population of individuals, or prediction algorithms.

This process is repeated until optimum fitness is reached 423. Such optimum fitness can be, for example, when a fitness score (defined, for example, as a maximum or average within a given generation) tends to a maximum, when it reaches a previously defined upper limit, and/or when the evolution has proceeded for a defined number of generations.

One or more individuals, i.e. prediction algorithms, with the best fitness score can then be selected and the corresponding distributions of records 425 on the training data subset and on the testing data subset may be used to train and test prediction algorithms for the problem under investigation.

The distribution of records 425 on the training and the testing subsets can be defined, for example, as a status vector. Such status vector has a dimensionality or length equal to the number of records N in the complete database 401, and each component of the vector can have one of two possible values, for example, 0 and 1. Each status vector component indicates assignment of that record to one of the two data subsets, namely the training or the testing subset. Thus, for example, if N=8 and the status variable is defined as 1 for training and 0 for testing, a value of 1010 1010 indicates records 1, 3, 5 and 7 being assigned to training subset and records 2, 4, 6 and 8 being assigned to the testing subset.

Figure 5:
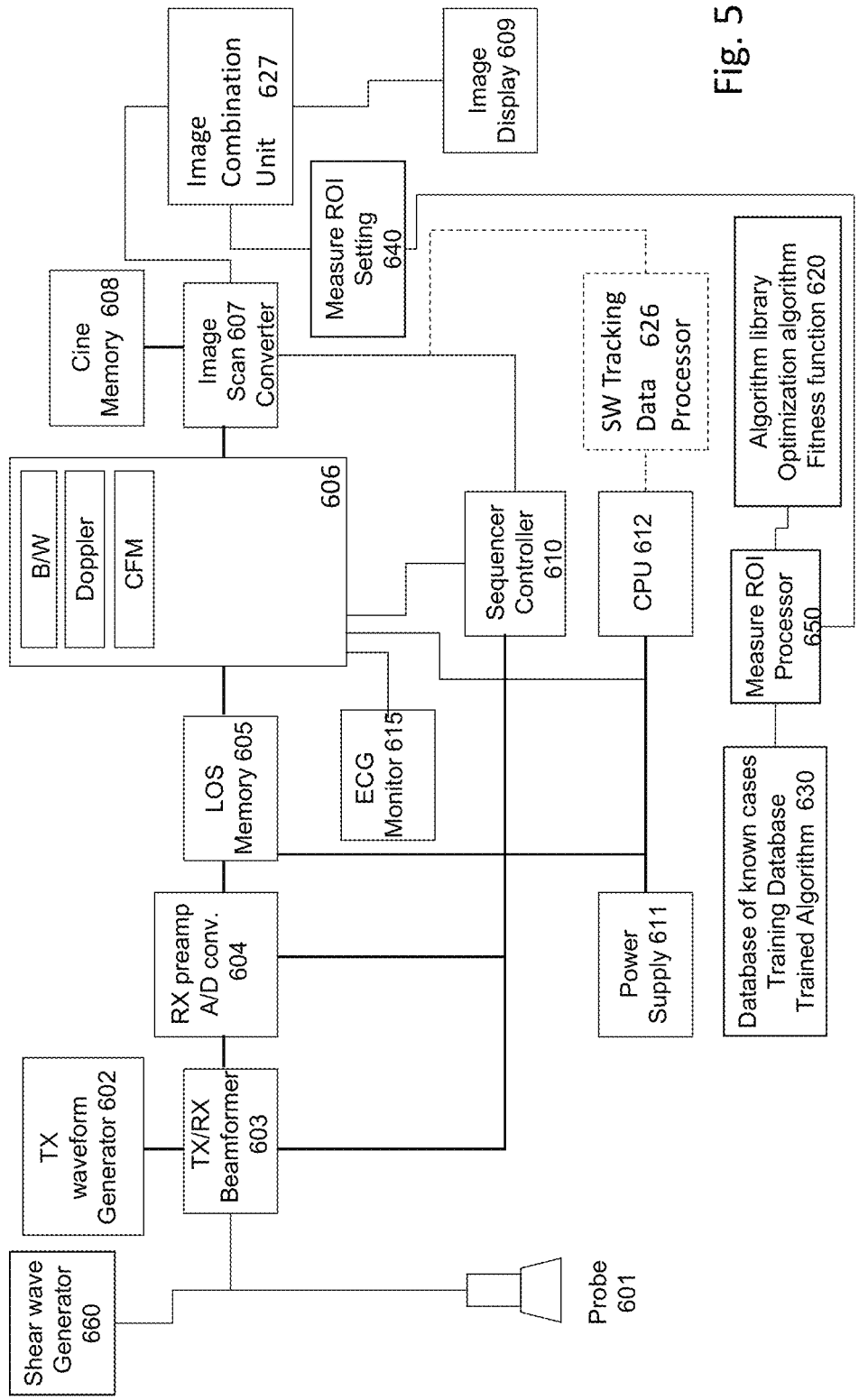
FIG. 5 show a high-level block diagram of an ultrasound system for carrying out shear wave elasticity imaging.

FIG. 5 illustrates a high-level block diagram of an ultrasound system. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 5 includes one or more ultrasound probes 601. The probe 601 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 601 is coupled over a wired or wireless link to a beamformer 603. The beamformer 603 includes a transmit (TX) beamformer and a receive (RX) beamformer that are jointly represented by TX/RX beamformer 603. The beamformer 603 supplies transmit signals to the probe 601 and performs beamforming of "echo" signals that are received by the probe 601.

A TX waveform generator 602 is coupled to the beamformer 603 and generates the transmit signals that are supplied from the beamformer 603 to the probe 601. The transmit signals may represent various types of ultrasound TX signals such as used in connection with B-mode imaging, colour Doppler imaging, pulse-inversion transmit techniques, contrast-based imaging, M-mode imaging and the like. In accordance with embodiments herein, the transmit signals include acoustic disturbance ultrasound (ACU) beam (10, in FIG. 1A) that are directed at select excitation points or regions (1 in FIG. 1A). The ACU beams are configured to generate shear waves as described herein.

The beamformer 603 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 604. The RF beamformed signals are converted to I, Q data pairs.

The TX waveform generator 902, TX/RX beamformer 603 and A/D converter 604 cooperate to generate the acoustic disturbance ultrasound beams (10) directed at the excitation point (1). The acoustic disturbance ultrasound beams are configured to produce shear waves (11) that have directions of propagation extending laterally from the directions of propagation of the acoustic disturbance ultrasound beams (10). The I, Q data pairs are saved as image pixels in the line of sight (LOS) memory. For example, the LOS memory may include LOS memory portions associated with each line of sight through the ROI. The I, Q data pairs, defining the image pixels for corresponding individual ROI locations along a corresponding LOS, are saved in the correspond LOS memory portion. A collection of image pixels (e.g., I, Q data pairs) are collected over time and saved in the LOS memory 605. The image pixels correspond to tissue and other anatomy within the ROI. As the ROI experiences the shear waves, the tissue and other anatomy in the ROI moves in response to the shear waves. The collection of image pixels captures the movement of tissue other anatomy within the ROI.

In embodiments herein, a dedicated sequencer/timing controller 610 may be programmed to manage acquisition timing which can be generalized as a sequence of firings aimed to locally generate shear waves aside the measurement box followed by tracking firings to monitor transition of the shear waves through the acquisition lines (LOS) in the measurement box (corresponding to the ROI). Optionally, idle phases can be added to control heating of the probe and manage compliance with safety emission regulations.

A sequence controller 610 manages operation of the TX/RX beamformer 603 and the A/D converter 604 in connection with transmitting ADU beams and measuring image pixels at individual LOS locations along the lines of sight. The sequence controller 610 manages collection of reference measurements and shear-wave induced measurements. The sequence controller 610 provides a pause period between a last measurement along one tracking line coincident with one line of sight and a first measurement along a following tracking line coincident with a following line of sight.

One or more processors 606 perform various processing operations as described herein. The CPU 612 may perform one or more of the operations described herein in connection with generation of shear waves, measurement of displacement, calculation of displacement speed, calculation of stiffness values and the like.

Among other things, the processor 606 and/or CPU 612 analyse the image pixels to measure displacement of the image pixels or controls an optional dedicated shear wave tracking data processor 626. The processor 606 and/or the CPU 612 and or the optional shear wave data processor measure the displacement at image pixels for the plurality of lines of sight placed in the region of interest. The lines of sight are located at different predetermined laterally staggered distances from the excitation point (1), (4).

The processor 606 and/or CPU 612 or optionally a dedicated shear wave tracking data processor 626 also calculates a stiffness value based on the speed of the shear wave according to one or more of the examples describe above.

Figure 6:
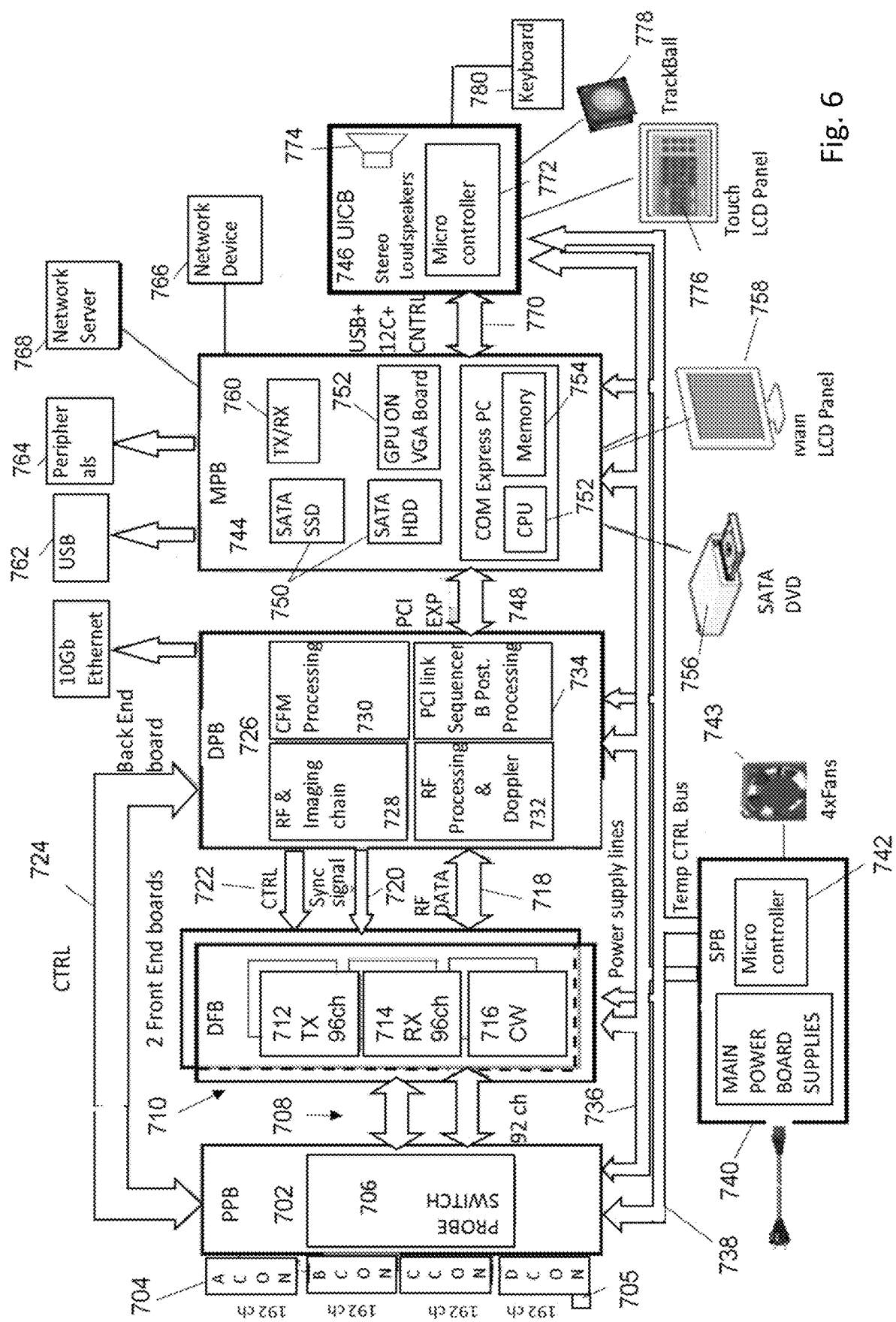
FIG. 6 illustrates a block diagram of an ultrasound system formed in accordance with an alternative embodiment.

According to an embodiment, the ultrasound system of FIG. 6 is provided with an integrated measure ROI automatic definition and setting unit. This unit can be constituted partly by software coding the instructions for enabling existing processors and the relating peripherals of the ultrasound system to carry out the functions of one or more units needed to carry out the method according to an example embodiment of the present invention and to one or more of the embodiments described above and partly by dedicated hardware combined with the said software.

Alternatively the said measure ROI automatic definition and setting unit may be entirely constituted by software coding the instructions for enabling existing processors and the relating peripherals of the ultrasound system to carry out the functions of one or more units needed to carry out the method according to embodiments herein or according to a further variant the said unit cam be entirely a hardware unit.

The embodiment shown comprises a processing unit of the measure ROI 650 which controls memories 630 and 620 respectively for storing the database of known cases and the optimized training database as well as the trained algorithm or algorithms and a a library of processing algorithms as well as of optimization algorithm and of fitness function. The output of the processor 650 sends the output data relating to the dimensions and to the position of the measure ROI to a measure ROI setting unit 640 which automatically sets the shear wave generator 660 to send excitation pulses of shear waves in the said measure ROI and also automatically controls the SW tracking processor 626 to carry out the tracking of the propagation of the shear wave inside the set measure ROI.

The results in terms of the position and the boundaries of the measure ROI can be displayed overlaid over the B-mode image. The elasticity data or the velocity data can be displayed by showing the numerical data and/or by giving to the pixels inside the measure ROI a colour of a colour palette scale used as a metric for the elasticity and/o velocity parameter.

As explained herein, the processor 606 and/or CPU 612 or the dedicated processor 626 obtaining one or more reference measurements for a plurality of lines of sight in the region of interest, prior to generating the first and second shear waves. According to an embodiment, the processor 606 and/or CPU 612 or the optional dedicated processor 626 measure the shear waves (11 include measuring mean displacement over time of the tissue along a plurality of line of sights and identifying a peak of the mean displacements.

For example, the measurements by the processor 606 and/or CPU 612 or the optional dedicated processor 626 may include calculating a cross-correlation between the measurements associated with the shear waves and a reference measurement obtained independent of the shear waves. The processor 606 and/or CPU 612 or the optional dedicated processor 626 measure displacement over time of the tissue along a plurality of line of sights and calculates speeds of the shear waves (11) based, in part, on distances of the corresponding lines of sight from the excitation point (1).

The processor 606 and/or CPU 612 also performs conventional ultrasound operations. For example, the processor 606 executes a B/W module to generate B-mode images. The processor 606 and/or CPU 612 executes a Doppler module to generate Doppler images. The processor executes a Color flow module (CFM) to generate colour flow images. The processor 606 and/or CPU 612 may implement additional ultrasound imaging and measurement operations. Optionally, the processor 606 and/or CPU 612 may filter the displacements to eliminate movement-related artifacts.

An image scan converter 607 performs scan conversion on the image pixels to convert the format of the image pixels from the coordinate system of the ultrasound acquisition signal path (e.g., the beamformer, etc.) and the coordinate system of the display. For example, the scan converter 607 may convert the image pixels from polar coordinates to Cartesian coordinates for image frames.

A cine memory 608 stores a collection of image frames over time. The image frames may be stored formatted in polar coordinates, Cartesian coordinates or another coordinate system.

An image display 609 displays various ultrasound information, such as the image frames and information measured in accordance with embodiments herein. For example, the image display 609 displays the stiffness values, displacement measurements, displacement speeds, and other information calculated in accordance with embodiments herein. The stiffness values, displacement measurements, displacement speeds, and other information may be displayed as image information, as numeric values, graphical information and the like. The display 609 displays the ultrasound image with the region of interest shown. Optionally, the display 609 may display indicia indicating the excitation points (1), where the indicia are overlaid on the ultrasound image and/or presented along opposite sides of the ultrasound image.

Optionally, the system of FIG. 5 may include an ECG monitor 615 that couples an ECG sensor to the patient and records an ECG signal indicative of the patient's heart rate. The processor 606 and/or sequence controller 610 synchronize the generation of acoustic disturbance ultrasound beams (10) and the measurement of the first and second displacements of the image pixels induced by the first and second shear waves (11) with the ECG signal.

The blocks/modules illustrated in FIG. 5 can be implemented with dedicated hardware (DPSs, FPGAs, memories) and/or in software with one or more processors.

A control CPU module 612 is configured to perform various tasks such as implementing the user/interface and overall system configuration/control. In case of fully software implementation of the ultrasound signal path, the processing node usually hosts also the functions of the control CPU.

A power supply circuit 611 is provided to supply power to the various circuits, modules, processors, memory components, and the like. The power front-end may be an A. C. power source and/or a battery power source (e.g., in connection with portable operation).

Optionally, in point Shear Wave acquisition, the RX tracking lines (line of sights-LOSs) may be temporarily stored, either as pure RF or as I/Q data, in the front-end local memories. The processing may be implemented by a dedicated processor module 606 and/or a CPU 612. Processed data may be formatted as shear wave speed measurements or stiffness values. These are then added to the ancillary data of the field-of-view under scan and properly reported as an overlay to the image displayed on system's monitor.

According to a further feature, an image combination unit 627 may be present in which the B-mode image data of at least of a region of interest and the corresponding graphic representation as an image of the velocity of the shear wave or of the elasticity parameter determined from said velocity data is combined for the superimposed display of the B-mode image and of the image representing the shear wave velocity and/or the elasticity features determined for the corresponding pixels in the B-mode image. The representation as an image of the velocity or of the corresponding elasticity parameter values and the combination of this image with the B-mode image can be carried out according to one of the previously disclosed methods.

FIG. 6 illustrates a block diagram of an ultrasound system formed in accordance with an alternative embodiment. The system of FIG. 6 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynaecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled connection port to the 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front-end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front-end boards 710 include transmit driver circuits 712 that generate transmit signals that are passed over corresponding to channels the corresponding transducers in connection with ultrasound transmit firing operations. The transmit driver circuits 712 provide pulse or control for each drive signal and transmit beamforming to management steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front-end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front-end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, as such control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front-end boards 710 may convert the RF ultrasound data to I, Q data pairs which are then passed to the digital processing board 726.

The digital processing board 726 includes an RF and imaging module 728, a colour flow processing module 730, an RF processing and Doppler module 732 and a PCI link module 734. The digital processing board 726 performs RF filtering and processing, processing of black and white image information, processing in connection with colour flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAS, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I, Q data pairs, and performs Doppler related processing on the I, Q data pairs. Optionally, the imaging module 728 may perform B mode related image processing upon I, Q data pairs. The CFM processing module 730 performs colour flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 7:
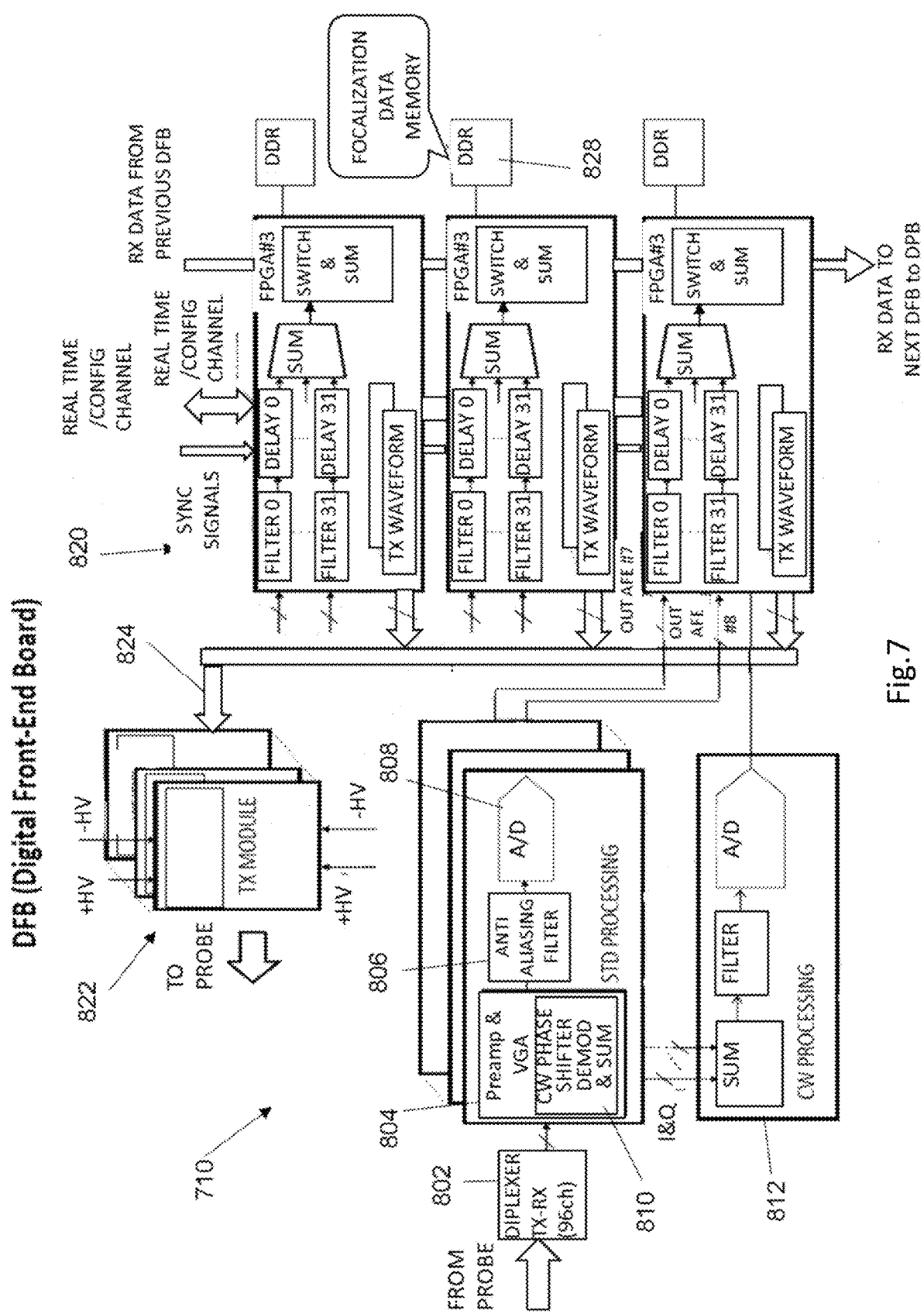
FIG. 7 illustrates a block diagram of a portion of the digital front-end boards.
Figure 9A:
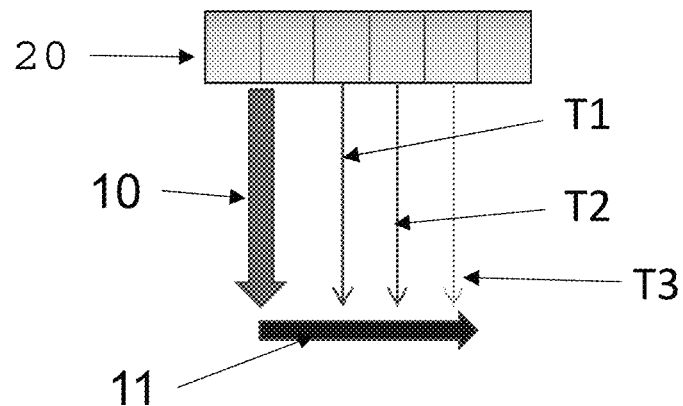
FIGS. 9A to 9C are diagrams representing in a simplified way a theoretical method of determining the velocity of the shear wave propagation in a region of interest according to the one-dimensional shear wave elasticity imaging mode.
Figure 9B:
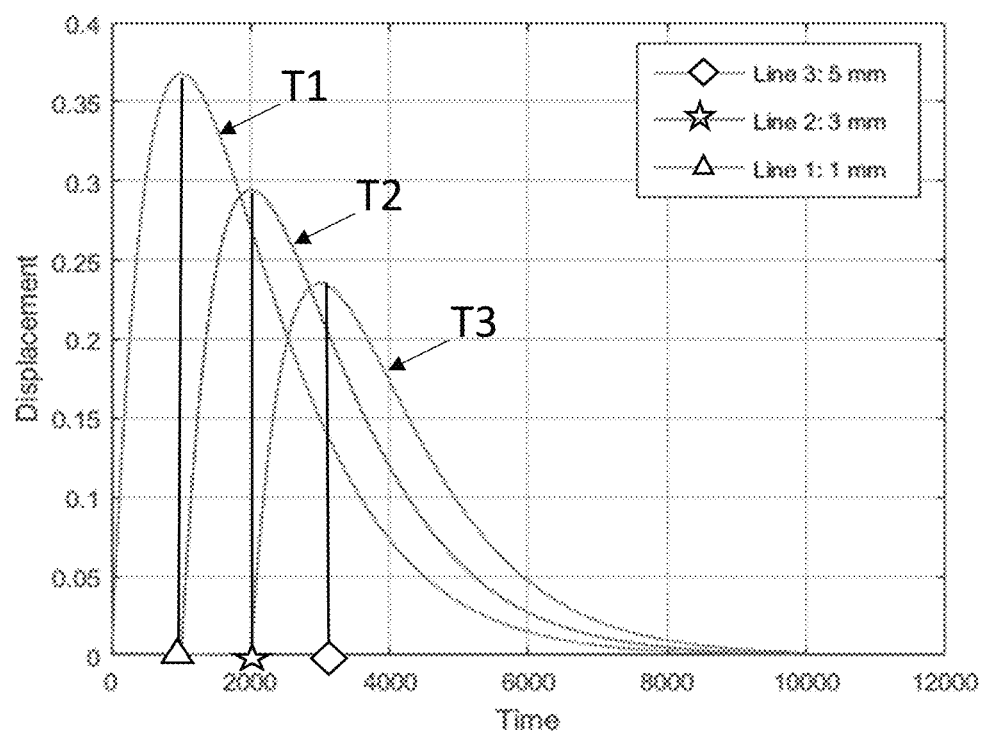
Figure 9C:
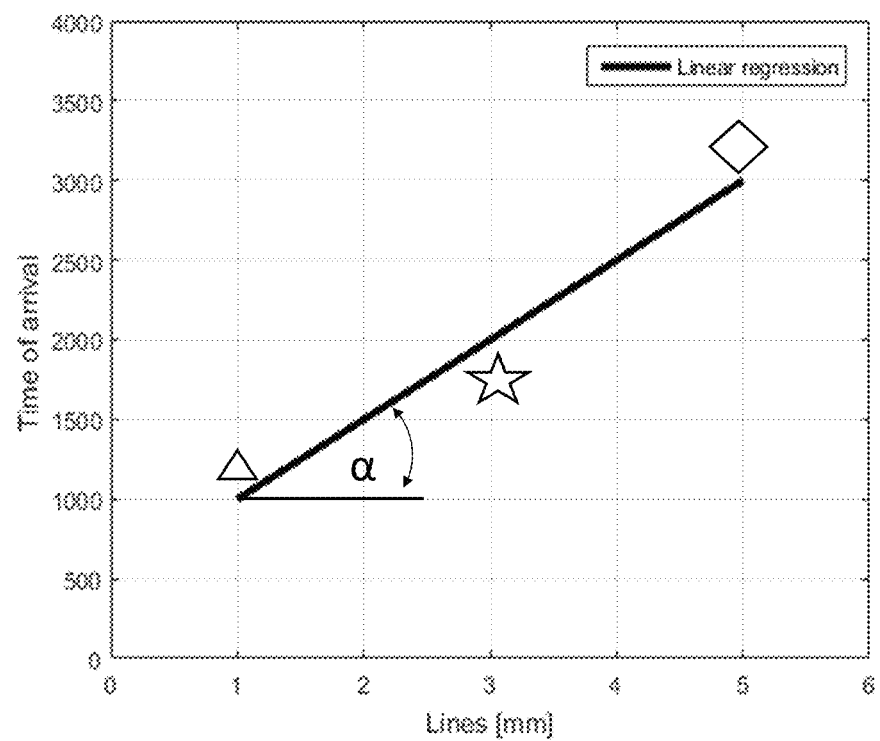

FIG. 7 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment the retrospective transmit beam focusing according to an example embodiment of the present invention may be applied to the RF data directly acquired by the system or to transformed data according to different transformations as for example as a phase/quadrature (I/Q) transformation, or similar.

In the embodiment of FIG. 7 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I, Q data pairs. The CW I, Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 726 (FIG. 8). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 (FIG. 7) also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

FIG. 8 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs colour flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally, or alternatively, the controllers and the controller device may represent circuitry that may be implemented as hardware. The above examples are exemplary only and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C#or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for two-dimensional shear wave elastography imaging (SWEI) comprising:
   a) Acquiring at least one B-mode ultrasound image of a region in a body under examination;
   b) Selecting an area of the B-mode image (image ROI) by placing a selection box on the B-mode image;
   c) Automatically acquiring two-dimensional shear wave elastography imaging data related to the selected area;
   d) Displaying an elasticity/velocity map on the selected area and optionally a reliability map;
   e) Providing an algorithm
   taking as input one or a combination of two or more of the data sets selected from a list consisting of: the B-mode raw data inside the selected area, the B-mode image data inside the selected area, the elasticity/velocity map inside the selected area, the reliability map inside the selected area, the raw two-dimensional shear wave elastography imaging data inside the selected area, the two-dimensional shear wave elastography imaging data at an intermediate stage of processing corresponding to at least one of displacement curves over time, and one or more peak features of the displacement curves selected from peak height, peak width, and peak position in time
   and providing as output at least the 2D coordinate of the center of a measure ROI and optionally the size and the shape of such measure ROI;
   f) Automatically displaying the measure ROI overlapped on the B-mode image and/or on the elasticity map and/or on the reliability map;
   g) Optionally tuning the measure ROI position, size and shape by receiving a user input;
   h) Computing an elasticity parameter corresponding to average elasticity, inside the measure ROI;
   i) Optionally weighting the elasticity parameter by the values of the reliability map;
   j) Displaying and/or saving the computed elasticity parameter in a memory.

2. A method according to claim 1, wherein the algorithm is selected among machine learning algorithms which are trained on known records relatively to known cases of measure ROI selection in SWEI imaging, each record comprising a 2D coordinate of the center of the measure ROI and, optionally, the size and the shape of the measure ROI associated to one or a combination of two or more data sets selected from the list consisting of: the B-mode raw data inside the selected area, the B-mode image data inside the selected area, the elasticity/velocity map inside the selected area, the reliability map inside the selected area, the raw SWEI 2D data inside the selected area, the SWEI 2D data at an intermediate stage of processing corresponding to at least one of the displacement curves over time and one or more of the peak features of the displacement curves selected from the peak height, the peak width, and the peak position in time.

3. A method according to claim 2, wherein the machine learning algorithm is a classification algorithm.

4. A method according to claim 2, wherein the algorithm is trained with a training database which has been subjected to a filtering and/or optimizing process.

5. A method according to claim 1, wherein the image data of the image ROI or of the B-mode image used as input data of the algorithm consists in one or more parameters describing the appearance of a pixel in the B-mode image, while the output data consist in data describing the dimensions and the position of the measure ROI in the B-mode image or in an image ROI selected in the B-mode image.

6. A method according to claim 5, wherein the parameters representing the feature of the pixels of the B-mode image or of an image ROI of the B-mode image and selected as an input of the algorithm comprises also one or more parameters representing the features of one or more surrounding pixel optionally weighted as a function of their distance from the pixel which is coded.

7. A method according to claim 1, wherein the algorithm is in the form of an analytic function selected from an optimization algorithm or a cost function to be minimized or maximized.

8. A method according to claim 7, wherein the cost function to be minimized is the number of outliers in relation to a regression line calculated as a function of the displacement peaks of pixels in said measure ROI induced by the passage of the shear wave and the position of the tracking lines of the shear wave propagation in said measure ROI.

9. A method according to claim 7, wherein the cost function to be maximized is the mean reliability of the elasticity or velocity data calculated in the measure ROI.

10. A method according to claim 7, wherein the cost function to be maximized is the Signal to Noise Ratio of the data of one or a combination of two or more of the data sets selected from the list consisting of: the B-mode raw data inside the image ROI, the B-mode image data inside the image ROI, the elasticity/velocity map inside the image ROI, the reliability map inside the image ROI, the raw SWEI data inside the image ROI, the SWEI data at an intermediate stage of processing corresponding to at least one of the displacement curves over time and one or more of the peak features of the displacement curves selected from the peak height, the peak width, and the peak position in time in the measure ROI.

11. A method according to claim 1, wherein the elasticity parameter determined from the automatic selected measure ROI is displayed together with a reliability parameter and/or together with the representation of the limits of the measure ROI.

12. An ultrasound system for shear wave elasticity imaging (SWEI) comprising:
an ultrasound probe;
an ultrasound transmit-wave generator and an ultrasound transmit beamformer;
an ultrasound receive beamformer;
ultrasound receive signals processing unit for generating ultrasound image data;
a shear wave excitation pulse generator and a shear wave beamformer;
a display for displaying an image;
a selection tool for selecting a region of the image (image ROI) by showing the limits of the said region on the said image on the display;
a central control unit comprising:
a memory storing program instructions;
at least one processor that executes the program instructions to:
 a) automatically acquire SWEI data related to the selected region by:
generating an acoustic excitation ultrasound pulse directed at an excitation region or point beside or inside the said image ROI, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;
 generating ultrasound tracking beams focused along different tracking lines which are at different predetermined laterally staggered distances one from the other and from the said excitation region or point and which encompasses the image ROI;
 processing the ultrasound echo signal reflected at different tracking focal points distributed along said tracking lines for calculating the values of elasticity parameters in the image ROI;
 b) Display an elasticity/velocity map on the image ROI and optionally a reliability map;
 c) carry out an algorithm taking as input one or the combination of two or more datasets selected from a list consisting of: the B-mode raw data inside the image ROI, the B-mode image data inside the image ROI, the elasticity/velocity map inside the image ROI, the reliability map inside the image ROI, the raw SWEI 2D data inside the image ROI, the SWEI 2D data at an intermediate stage of processing corresponding to at least one of displacement curves over time, and one or more peak features of the displacement curves selected from peak height, peak width, and peak position in time, and providing as output at least the 2D coordinate of the center of a measure ROI and optionally the size and the shape of such measure ROI;
 d) Automatically display the measure ROI overlapped on the B-mode image and/or on the elasticity map and/or on the reliability map;
 e) Optionally tune the measure ROI position, size and shape upon user input;
 f) Compute the average elasticity inside the measure ROI;
 g) optionally weight the average elasticity by the values of the reliability map;
 h) Display and/or save the computed average elasticity in a memory.

13. An ultrasound system according to claim 12 further comprising:
an image generation unit for graphically representing the elasticity parameter values in the selected measure ROI in an elasticity image;
an image combination unit for combining the image elasticity image with the anatomic B-mode image of the said selected measure ROI;
an image display receiving the image data from the image combination unit and displaying the combined image.

* * * * *